(12) United States Patent
Ruse

(10) Patent No.: US 7,983,748 B2
(45) Date of Patent: Jul. 19, 2011

(54) APPARATUS AND METHOD FOR TREATING ATRIAL FIBRILLATION AND ATRIAL TACHYCARDIA

(76) Inventor: Richard B. Ruse, Atlanta, GA (US)

( * ) Notice: Subject to any disclaimer, the term of this patent is extended or adjusted under 35 U.S.C. 154(b) by 135 days.

(21) Appl. No.: 12/393,899

(22) Filed: Feb. 26, 2009

(65) Prior Publication Data

US 2009/0216290 A1 Aug. 27, 2009

Related U.S. Application Data

(60) Provisional application No. 61/031,486, filed on Feb. 26, 2008.

(51) Int. Cl.
*A61N 1/00* (2006.01)
(52) U.S. Cl. .......................................................... 607/2
(58) Field of Classification Search ................ 607/2, 14, 607/44, 45, 9; 600/509
See application file for complete search history.

(56) References Cited

U.S. PATENT DOCUMENTS

| 7,555,341 | B2 * | 6/2009 | Moffitt et al. .................... 607/14 |
| 7,647,115 | B2 * | 1/2010 | Levin et al. ...................... 607/44 |
| 7,657,310 | B2 * | 2/2010 | Buras ................................ 607/2 |
| 2003/0045909 | A1 * | 3/2003 | Gross et al. ........................ 607/9 |
| 2008/0103440 | A1 * | 5/2008 | Ferren et al. ............... 604/95.01 |

* cited by examiner

*Primary Examiner* — George Manuel
*Assistant Examiner* — Robert N Wieland
(74) *Attorney, Agent, or Firm* — William H. Dippert; Eckert Seamans Cherin & Mellott, LLC

(57) ABSTRACT

A method and device for treating an electrical problem in an organ, especially a heart, of a human or animal patient comprises atraumatically blocking the transmission of one or more electrical signals external to the organ. Nerve cell membranes near a cathode are depolarized while nerve cell membranes near an anode are hyperpolarized, inducing a DC conduction block. The method and device are especially suitable for treating atrial tachycardia where unwanted signals from at least one pulmonary vein and/or at least one fat pad are blocked within the construct of the heart.

19 Claims, 11 Drawing Sheets

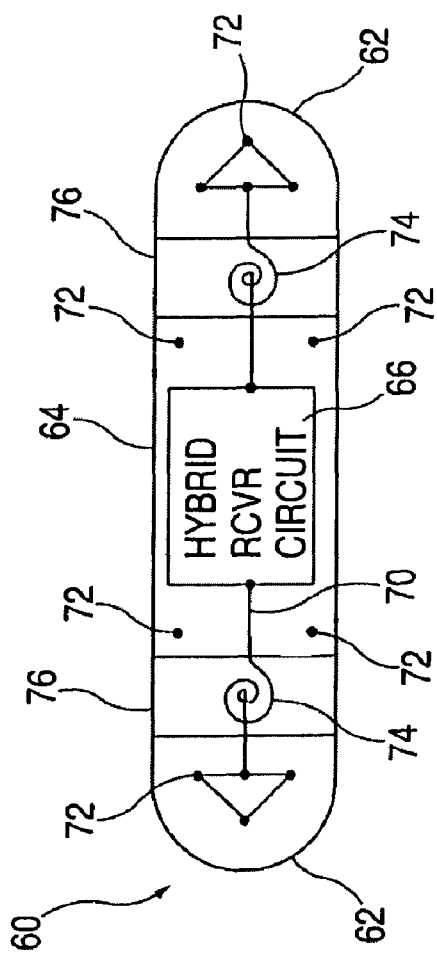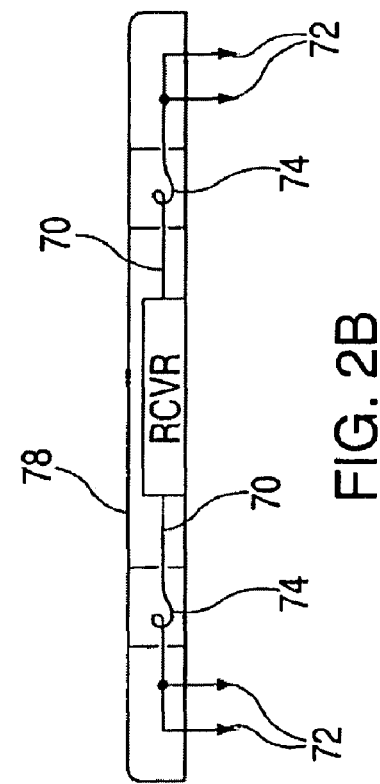
FIG. 2A
FIG. 2B

APPARATUS AND METHOD FOR TREATING ATRIAL FIBRILLATION AND ATRIAL TACHYCARDIA

CROSS-REFERENCE TO RELATED APPLICATION

This application is based upon and claims the benefit of the filing date of co-pending, commonly assigned U.S. Provisional Patent Application Ser. No. 61/031,486, filed Feb. 26, 2008, which is incorporated herein by reference in its entirety.

FIELD OF THE INVENTION

This invention relates to the treatment of atrial fibrillation [AF] and atrial tachycardia [AT]. More particularly, this invention relates to a method for treating atrial fibrillation or atrial tachycardia which is comprised of a direct current [DC] conduction block to cancel the noise emanating from the pulmonary veins in the left atrium sufficiently to halt AF or AT.

BACKGROUND OF THE INVENTION

Fast atrial arrhythmias such as AF and AT are abnormal heart rhythms which afflict around three million people each year in the United States. The most prevalent evidence of the disease electrically is a preponderance of irregular AF wavelets of activation that is frequently generated in the pulmonary veins [PVs] and is conducted into the left atrium and then the right atrium causing chaotic and rapid activation that interferes with the normal SA/AV cardiac electrical pathways and causes rapid, irregular ventricular contractions. These atrial tachycardias can be in the form of atrial fibrillation or atrial flutters, typical and atypical, which may vary in terms of severity and rate. AF makes the ventricular response so irregular and fast that it interferes with normal blood flow through the heart chambers, can lead to severe structural heart disease, and can be life-threatening if not treated effectively. While the irregular rate of ventricular contraction during AF and AT may compromise cardiac output and cause fatigue, much of the increased mortality associated with AF is due to clot formation due to the poor circulation in the atria that embolizes to cause stroke, renal infarcts, etc. Persistent AF over weeks or months is particularly dangerous.

There are a number of known modalities for treating atrial tachycardias. The "Maze Procedure" was developed many years ago and affects a cure rate of at least 90% for AF. This procedure involves "cutting" surgical lines or patterns in the right and left atria [RA and LA] to interrupt unwanted conduction pathways that cause AF. The drawback to this procedure is that it requires open heart surgery and is usually performed on a patient only if there is another more important reason to enter the heart via major surgery, such as a valve replacement or a similar procedure.

RF/microwave ablation, cryo-ablation, ultrasound ablation, or variants of the Maze Procedure are used to burn, freeze, or cut and score lines in the right and left atria. Ablation is performed inside or just outside the pulmonary veins (PVs) and ostia in an attempt to interrupt sources of activation wavefronts that arise in the PVs and propagate into the atria and lead to AF and AT. There is strong empirical evidence that micro-re-entrant electrical signals emanate from the lungs via the pulmonary vein nerve cables and conduct unwanted wavelet noise signals into the LA and RA that are largely responsible for AF. Other points of interest within the left atrium of the heart that are targets of RF ablation procedures are the ostia and ganglionated plexi. The left atrial appendage and Ligament of Marshall may also be removed epicardially via limited thoracotomy to remove unwanted circuit pathways and to prevent clots from forming [left atrial appendage].

There are concerns and known side effects such as esophageal fistulae and stenosis of the PV ostia as a result of these ablation procedures. Each case is unique in that there are infinite combinations of tissue conduction pathways and electro-physiologic anomalies and differences within each person that cause the wavelet trains that cause AF and atrial flutter. Knowing where to ablate the tissues of interest is difficult, at best. Also, the cure rate is less than optimum for persons with chronic AF and severe structural heart disease as compared to persons with paroxysmal or occasional/idiopathic AF/flutter. It is also difficult to make the long ablation lesions continuous and transmural.

Another procedure to treat AF tachycardia is DC cardioversion shock therapy to convert AF/flutter to sinus rhythm. This is an excellent conversion tool; however, unless the underlying cause of the AF is resolved, it most likely will recur. Implantable cardioverter defibrillators [ICDs] have been used for conversion of AF, but since the patient is conscious when the shock is delivered, many individuals find the discomfort of the shock intolerable. These systems generally use a "hot can" approach where a very high voltage and current are delivered through the heart and the left chest and pectoral areas, causing significant pain during a defibrillation or cardioversion shock. One advantage of an ICD with AF cardioversion capability is to reduce the amount of time that AF persists before cardioversion to reduce the risk of clot formation.

Anti-arrhythmia drug therapy is effective in many cases even if the AF is not entirely converted back to a normal sinus rhythm. A primary cause for concern is that these drugs are systemic and affect other systems such as the liver, kidneys, and heart, and can also cause fatigue associated with loading and maintenance doses of these drugs.

In patients who do not respond to medications and who are not good candidates for the previous methods for curing or controlling AF, the AV node may be ablated to create complete heart block so that the rapid, irregular atrial activations do not propagate to the ventricles and a pacemaker is implanted to control the heart's rate and rhythm. Drawbacks with the use of pacemakers include possible lead fractures and the abnormal activation sequence they cause in the ventricles, which leads to an abnormal contraction sequence and decreased ventricular function.

Thrombolytic drugs in conjunction with anti-arrhythmic drugs are valuable to prevent thromboembolisms and slow the heart rate. However, long term use of thrombolytic agents may have side effects that can be serious such as hemorrhage.

OBJECTS OF THE INVENTION

It is an object of the invention to provide electrical management of cardiac arrhythmias or abnormal heart rhythms that occur in the atria of the human heart.

It is also an object of the invention to provide treatment of atrial tachycardias such as atrial fibrillation and atrial flutters using an atraumatic and pain free method and device for converting and preventing atrial fibrillation and atrial flutters.

It is a further object of the invention to provide treatment of atrial tachycardias such as atrial fibrillation and atrial flutters.

It is a further object of the invention to provide successful management of atrial fibrillation and atrial flutters involving atrial or upper chambers of the human heart, using a unique electrical, direct current, noise blocking, and cancellation technology to "cancel" electrical wavefronts and noise signals to prevent them from propagating.

It is a further object of the invention to atraumatically block unwanted electrical signals emanating from a pulmonary vein and/or a fat pad.

It is a further object of the invention to provide a method for treating an atrial cardiac condition in a patient which comprises using a DC conduction block to cancel unwanted electrical signals emanating from a pulmonary vein and/or a fat pad.

It is a further object of the invention to provide a method of treating an atrial cardiac condition wherein the atrial cardiac condition is atrial tachycardia, atrial fibrillation, or atrial flutter.

It is a further object of the invention to provide a method of treating an atrial cardiac condition wherein the unwanted electrical signals interfere with electrical signals from an SA node and/or the atrial electrical conduction system.

It is a further object of the invention to provide a method of treating an atrial cardiac condition wherein the unwanted electrical signals emanate from at least one pulmonary vein in the left atrium, from at least one fat pad connected to the left atrium, or from at least one least one pulmonary vein and at least one fat pad connected to the left atrium.

It is a further object of the invention to provide a method of treating an atrial cardiac condition wherein at least one noise cancellation device is positioned on or adjacent to a pulmonary vein or a fat pad connected to the left atrium.

It is a further object of the invention to provide a method of treating an atrial cardiac condition wherein the noise cancellation device is a neurostimulator.

It is a further object of the invention to provide a system for treating a cardiac condition in a patient, which system comprises:
  an ECG sensing and control circuit;
  a transmitter for transmitting a signal; and
  at least one receiver for receiving said signal,
wherein each receiver is positioned on or adjacent to a pulmonary vein or fat pad and each receiver acts to cancel unwanted electrical signals from the pulmonary vein or fat pad.

It is a further object of the invention to provide a system for treating a cardiac condition in a patient, which comprises:
  a flexible circuit which is hard wired between the ECG sensing and control circuit and the targeted area for noise cancellation on the heart epicardially which is a direct wired approach as an alternative to the RF wireless or optical approaches.

It is a further object of the invention to provide a system for treating a cardiac condition which comprises:
  a magnetic neurostimulator [MNS] consisting of two fixed magnets and a traversing magnet which travels through a wire coil thereby inducing an electrical alternating current [AC] and voltage which is then rectified through a semiconductor diode or bridge rectifier and filtered by a small capacitor and comprises a direct current [DC] conduction blocking signal wherein each magnetic device is positioned on a pulmonary vein and each MNS acts to cancel unwanted electrical signals from a pulmonary vein.

It is a further object of the invention to provide a system for treating a cardiac condition which comprises:
  a system for blocking a nerve, where the nerve is blocked with DC stimulus, wherein the nerve cells near a cathode are depolarized and the nerve cells near an anode are hyperpolarized.

These and other objects of the invention will become more apparent in the discussion below.

SUMMARY OF THE INVENTION

According to the invention, atrial fibrillation and atrial flutters involving atria or upper chambers of the human heart are successfully managed using a unique electrical, direct current, noise blocking and cancellation technology. The device and method used according to the invention are considered to be atraumatic, that is, no ablation, burning, cutting, shocking or freezing. The device is intended to be used outside the construct of the heart so that this device does not interfere with motion or heartbeat activity. It is within the scope of the invention that the device could be used inside the construct of the heart in other applications.

Pulmonary veins comprise nerves, each of which is essentially a cable. A nerve can be blocked with a DC stimulus, wherein nerve cell membranes near a cathode are depolarized while the nerve cell membranes near an anode are hyperpolarized.

The goals and benefits of the technology of the invention are to prevent and convert with AF/AFL in an atraumatic method patients who have no hope of otherwise living with a normal sinus rhythm. Also, the technology eliminates severe DC shocks from defibrillation and eliminates or minimizes use of pharmaceuticals such as blood thinners and anti-arrhythmic drugs which have untoward side affects.

Electrical currents or noise external to a patient's heart are known to interfere with the transmission of electrical signals within the heart. More particularly, it is known that electrical signals or noise from pulmonary veins or fat pads adjacent to the left atrium of the heart can interfere with signals within the left and right atria, especially with electrical pulses or signals from the SA node conduction system. According to the invention, the unwanted noise signals from a pulmonary vein and/or fat pads as integral parts of the left atrium are blocked or redirected in an atraumatic manner. This treatment eliminates atrial fibrillation and atrial tachycardias where the origin of the arrhythmia is unwanted noise or electrical activity which emanates from the pulmonary veins and/or fat pads.

In one aspect of the invention, a wireless, RF/microwave neurostimulator transmitter/receiver device is set for prevention, soft conversion and long term control of atrial fibrillation and atrial flutter based upon a unique noise cancellation technique. This device uses transmitted RF/microwave energy that is converted to a DC voltage and current via simple and reliable receiver circuits which require no other internal power sources. When a coil of wire is wired in parallel with a capacitor, the circuit will resonate at a specified frequency when exposed to an RF energy source. The RF sinusoidal waveform created by the tuned circuit within the coil and capacitor are then rectified through a semiconductor diode or diode bridge which converts the alternating current [AC], high frequency signal into a direct current [DC] which is then filtered via a small capacitor. It is this direct current [DC] which forms the basis for the DC conduction block in the RF embodiment of the invention.

Advantageously the device of the invention is used for AF/AFL cases which are chronic with structural heart disease which do not respond to conventional pharmacological therapies or in which the structural geometries of the left atrium of the heart cannot safely undergo RF or other ablation therapy procedures. According to the invention an atraumatic, low power, DC voltage and current source is used for the purpose of blocking and attenuating the unwanted electrical noise or AF/AFL signal activity within the left atrium, pulmonary veins and the epicardial fat pads which are adjacent to or in close proximity to the pulmonary veins. Due to the lower source impedance of the DC voltage and current the receiver devices offer relative to the wavelet noise which emanates from the pulmonary veins, this technology is used to ensure targeting a definitive path between two points for canceling noise so heart muscle tissue cannot fibrillate or behave as during AF/AFL.

Pulsed AC or RF signals alone do not provide the ability to disrupt the signals and pathways of interest reliably. These signals simply "add or ride" on each other and will not cancel the unwanted AF/AFL noise in question. The DC voltage and current may be pulsed or strobed on and off at slightly higher power levels for intervention/conversion and then rolled back to a prevention/maintenance voltage and current level.

In another embodiment of the invention a fiber optic and or a light pipe is employed to energize a photocell, photo detector, phototransistor, photovoltaic device, light dependant resistor, or any other suitable optical device that will serve as a neurostimulator transmitter/DC receiver device for prevention, soft conversion, and long term control of atrial fibrillation and atrial flutters based around a very unique noise cancellation technique. This device uses transmitted light energy that is converted to a DC voltage and current via simple and reliable optical receiver circuits which require no other internal power sources. When an optical device such as a photocell is energized by a light source such as a light emitting diode [LED], the photocell will produce a small voltage and current which is used as a voltage and direct current conduction block which is useful to this invention.

Advantageously the device of the invention is used for AF/AFL cases which are chronic with structural heart disease which do not respond to conventional pharmacological therapies or where the structural geometries of the left atrium of the heart cannot safely undergo an RF or other ablation therapy procedure. This invention uses an atraumatic, low power, DC voltage and current source for the purpose of blocking and attenuating the unwanted electrical noise or AF signal activity within the left atrium, pulmonary veins and the epicardial fat pads which may be adjacent to or in close proximity to the pulmonary veins. Due to the lower source impedance of the DC voltage and current receiver devices this technology is used to ensure targeting a definitive path between two points for canceling noise so the heart muscle tissue cannot fibrillate or flutter as during AF/AFL. The DC voltage and current may be pulsed or strobed on and off at slightly higher power levels for intervention/conversion and then rolled back to a prevention/maintenance voltage and current level.

In one embodiment of the invention, a method for treating an electrical problem in an organ of a human or animal patient comprises atraumatically blocking the transmission of one or more electrical signals external to the organ.

In another embodiment of a method of the invention, nerve cell membranes near a cathode are depolarized while nerve cell membranes near an anode are hyperpolarized, inducing a DC conduction block.

In another embodiment of a method of the invention, the organ is the patient's heart.

In another embodiment of a method of the invention, electrical signals from a pulmonary vein, a fat pad, or a pulmonary vein and a fat pad are blocked from reaching the left atrium of the heart.

In another embodiment of a method of the invention, electrical signals are blocked by a DC current and/or voltage.

In another embodiment of a method of the invention, the DC current and/or voltage results from energy transmitted from an RF microwave, optical, or light energy source.

In another embodiment of a method of the invention, the DC current and/or voltage results from a neurostimulator.

In another embodiment of a method of the invention, the electrical signals are cancelled, redirected, or both.

In another embodiment of a method of the invention for treating atrial tachycardia in a patient's heart, electrical signals emanating from one or more pulmonary veins, one or more fat pads, or one or more pulmonary veins and one or more fat pads are atraumatically blocked.

In another embodiment of the invention, a system for carrying out a method of the invention comprises:
  a source of RF electromagnetic, light, or optical energy,
  a transmitter for transmitting said energy; and
  a receiver capable of receiving said energy and using said energy to block electrical signals external to the organ.

In another embodiment of the invention, a receiver causes DC current and/or voltage to block unwanted electrical signals.

In another embodiment of the invention, unwanted electrical signals are cancelled, directed away from the heart, or a combination thereof.

In another embodiment of the invention, a method for treating an atrial cardiac condition in a patient comprises using a DC conduction block to cancel unwanted electrical signals emanating from one or more pulmonary veins, one or more fat pads, or one or more pulmonary veins and one or more fat pads, wherein nerve cell membranes near a cathode are depolarized while the nerve cell membranes near an anode are hyperpolarized, inducing a DC conduction block.

In another embodiment of a method of the invention, the atrial cardiac condition is atrial tachycardia, atrial fibrillation, or atrial flutter.

In another embodiment of a method of the invention, the atrial flutter is typical atrial flutter or atypical atrial flutter.

In another embodiment of a method of the invention, unwanted electrical signals interfere with electrical signals from an SA node and/or the atrial electrical conduction system.

In another embodiment of a method of the invention, unwanted electrical signals emanate from at least one pulmonary vein in the left atrium, from at least one fat pad connected to the left atrium, or from at least one pulmonary vein in the left atrium and at least one fat pad connected to the left atrium.

In another embodiment of a method of the invention, at least one noise cancellation device is positioned on or adjacent to a pulmonary vein or a fat pad connected to the left atrium.

In another embodiment of a method of the invention, a noise cancellation device is a neurostimulator which induces a DC conduction block.

In another embodiment of the invention, a system for treating a cardiac condition in a patient comprises:
  an ECG sensing and control circuit;
  a transmitter for transmitting a signal; and
  at least one receiver for receiving said RF or optical signal,
  wherein each RF or optical receiver is positioned on or adjacent to a pulmonary vein or fat pad and each receiver acts to cancel unwanted electrical signals from the pulmonary vein or fat pad.

In another embodiment of the invention, a receiver is a neurostimulator.

In another embodiment of the invention, in a system for blocking a nerve, the nerve is blocked with DC stimulus, wherein the nerve cells near a cathode band or electrode are depolarized and the nerve cells near an anode band or electrode are hyperpolarized.

In another embodiment of the invention, the nerves are within and on the surface of pulmonary veins.

In another embodiment of the invention, a system for treating a cardiac condition in a patient comprises a flexible circuit which is hard wired between the ECG sensing and control circuit and the targeted area for noise cancellation on the heart epicardially.

In another embodiment of the invention, the hard wired ECG and control circuits are a neurostimulator.

In another embodiment of the invention, a system for treating a cardiac condition in a patient comprises a magnetic neurostimulator [MNS] comprising two fixed magnets and a traversing magnet which travels through a wire coil thereby inducing an electrical voltage and current which comprises a conduction blocking signal wherein each magnetic device is positioned on a pulmonary vein and each MNS acts to cancel unwanted electrical signals from the pulmonary vein.

In another embodiment of the invention, a system for treating a cardiac condition in a patient comprises one or more neurostimulators each positioned to block unwanted electrical signals that emanate from at least one pulmonary vein in the left atrium, from at least one fat pad connected to the left atrium, or from at least one pulmonary vein in the left atrium and at least one fat pad connected to the left atrium.

BRIEF DESCRIPTION OF THE DRAWINGS

FIGS. 2A and 2B represent top and lateral schematic representations, respectively, of an RF or optical receiver assembly useful according to the invention;

DETAILED DESCRIPTION OF THE INVENTION

One aspect of the invention is based upon the principle that the source impedance of a DC current blocking device, useful according to the invention, is much lower than the higher source impedance of the cardiac conduction electrical system within the heart. The tissue becomes the "resistive load" in the circuit. Thus, for the sake of discussion, if one injects a DC voltage at a contact point at least 10 times the voltage amplitude of the existing AF/AFL signals, unwanted AF/AFL signals will be electrically overpowered and trapped out back at the return of the circuit, at a second contact point. This device causes a small current pathway through the tissue of interest. More importantly, a nerve cable or bundle can be blocked with a DC stimulus and a nerve is basically a cable, so that the nerve cell membranes near a cathode are depolarized while the nerve cell membranes near an anode are hyperpolarized. This is a characteristic of nerves within the pulmonary veins.

The higher DC voltage amplitude would be from about 1 mV to about 500 mV as compared from about 10 μV to about 100 μV AF/AFL signals which have a frequency of from about 100 beats per minute [BPM] to about 600 BPM. The DC currents with these devices are expected to be in the micro-milliamp region, thereby not causing any harm to the tissues of interest. The DC current block therapy may be applied in a pulsed or synchronous fashion as to be timed to avoid normal "P" wave ECG activity and the pumping contribution from the left and right atria.

A few pins or contacts with anchors will be required to secure the receiver devices and will provide the electrical contact via platinum plated conduction contact pads and pins which will mechanically and electrically enter the myocardium and or the pulmonary veins. The goal is to "saturate" the cardiac tissue area with DC voltage and current pulses that will be programmed into the transmitter electronics to be in an "on or off state" during the desired time intervals.

A desirable characteristic of a DC current block is that it will override the AF/AFL noise signals of concern within the pulmonary veins and ostium within the LA. The hypothesis is that if a circulating DC current is flowing that is greater than the AF/AFL signals, the heart muscle tissue will not be able to oscillate or fibrillate and will be refractory to the unwanted signals. Also, by inducing a DC current through the tissues of interest, the new DC current pathways will provide an escape path for attenuating, dissipating and canceling the AF/AFL signals to adjacent tissues.

Figure 1A:
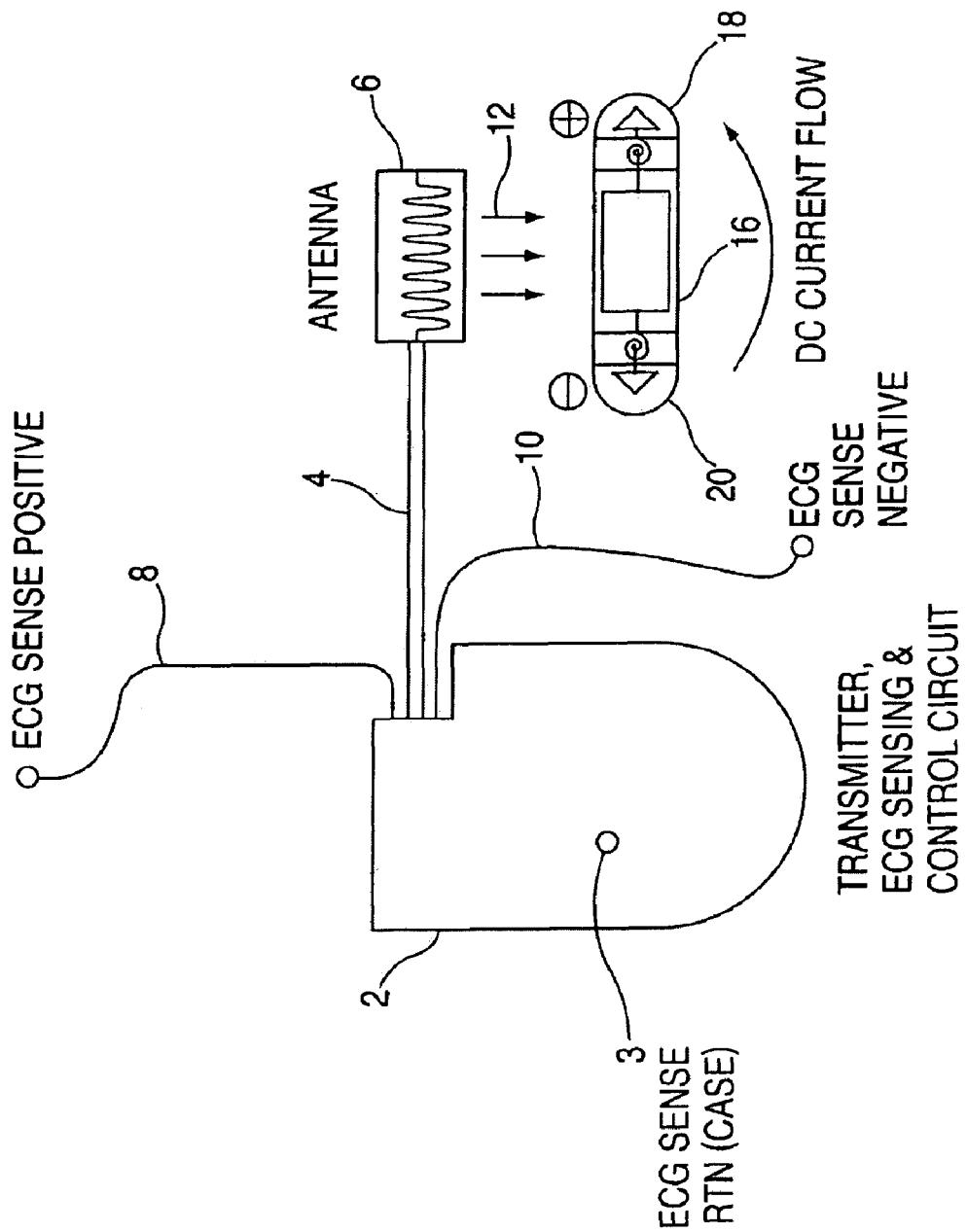
FIG. 1A is a schematic representation of an RF transmitter, ECG sensing and control circuit, and receiver useful according to the invention.
Figure 1B:
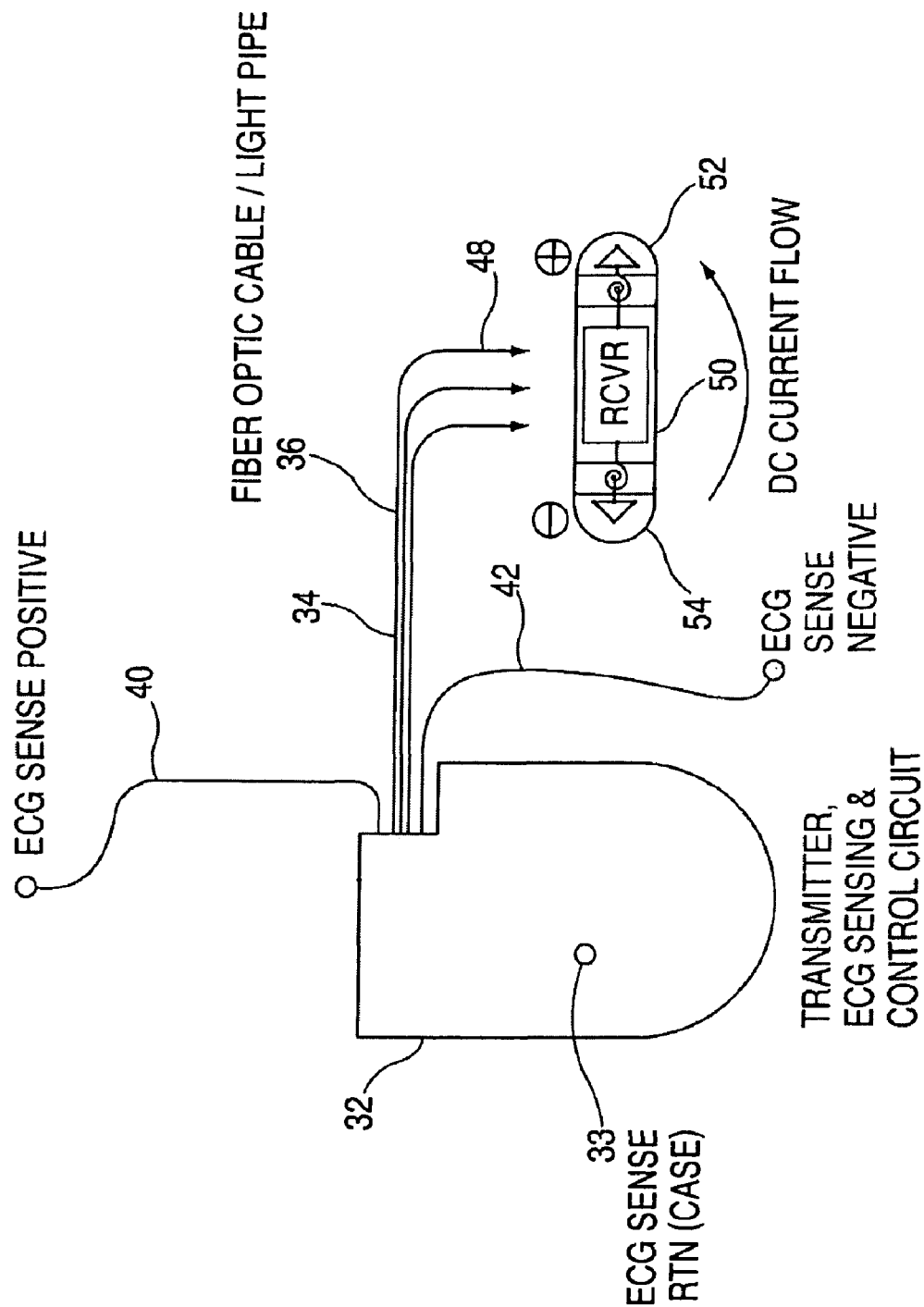
FIG. 1B is a schematic representation of an optical transmitter consisting of a light emitting diode [LED], ECG sensing and control circuit, and receiver useful according to the invention.

The invention can perhaps be better appreciated from the drawings. FIGS. 1A and 1B are schematic representations of RF wireless and optical system embodiments, respectively, of the invention. In FIG. 1A a transmitter 2 generates an RF/microwave signal that is transmitted through a cable 4 to an antenna 6. RF/microwave, transmitters, ECG sensing circuits, control circuits, and battery power supply are all located within transmitter case 3, which is positioned in the upper left shoulder area in the same location as an implantable cardiac defibrillator or pacemaker metal case. An ECG sense positive lead wire 8 and ECG sense negative lead wire 10 are installed subcutaneously by an electro-physiologist for standard ECG monitoring. The ECG sensing and control circuits interpret signals from lead wires 8 and 10 and deliver the DC conduction block commands to RF transmitter 2. RF transmitter case 3 serves as the ECG sensing circuit "ground" or "return" path.

Figure 4:
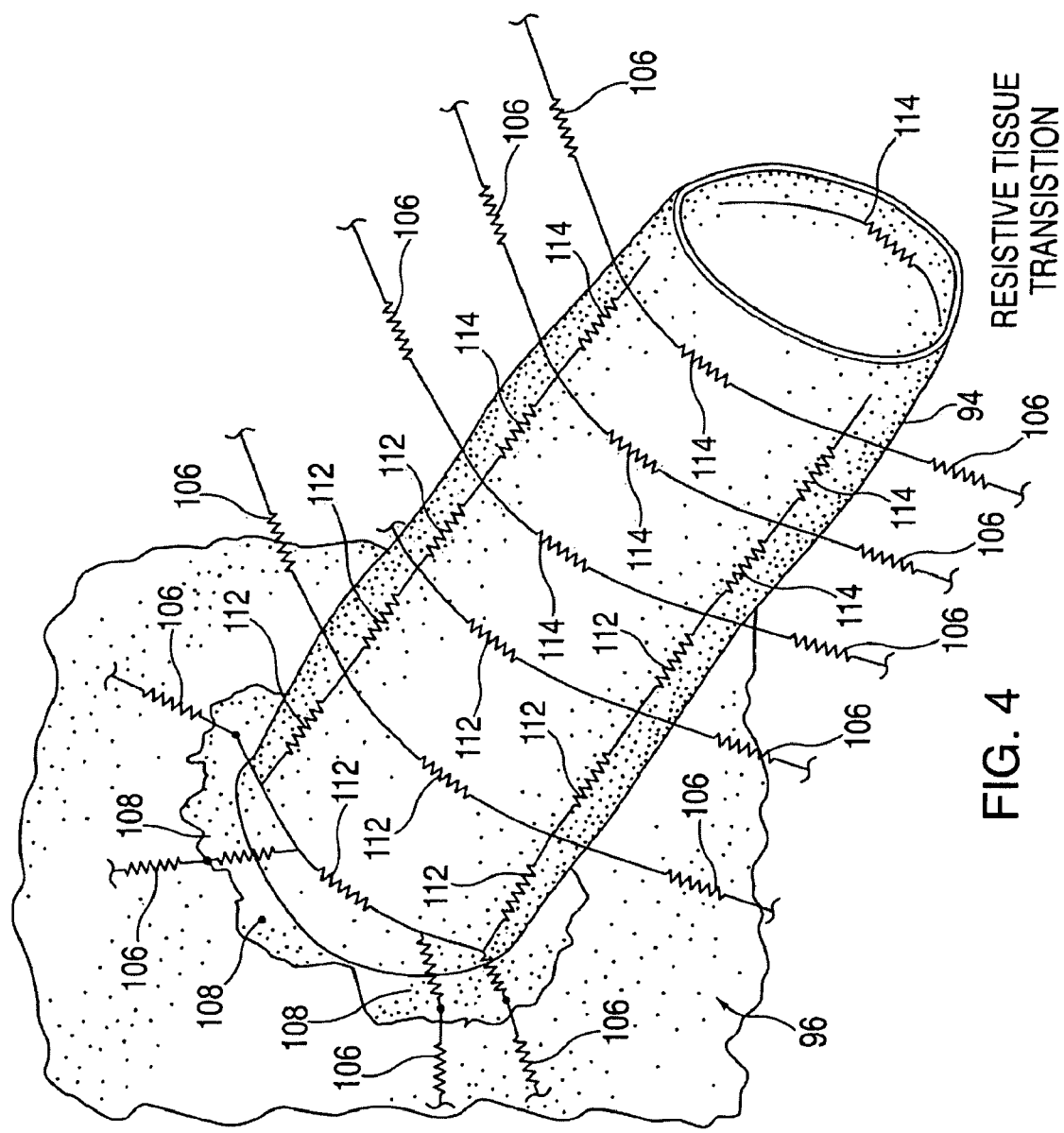
FIG. 4 is a schematic representation of the transition from heart muscle to pulmonary vein tissue within the construct of a pulmonary vein as well as adjacent body tissue resistances.

Antenna 6 generates an RF microwave signal 12 that is received by one or more DC receivers 16, which convert the RF/microwave energy to a direct current and voltage. A receiver 16 will be attached to or embedded in body tissue or heart muscle, such as shown in FIG. 4. Typically receiver 16 will have a positive section 18 and a negative section 20, and there will be DC current flow from positive section 18 to negative section 20 through body tissue or heart muscle, which forms "resistive load." In this embodiment, no batteries or other energy sources are required to deliver the DC conduction block at the sight of attachment.

In FIG. 1B, a transmitter 32 generates an optical signal that is transmitted through a cable 34 to a fiber optic or light pipe 36. The fiber optic or light pipe transmitters such as a light emitting diode [LED], ECG sensing circuits, control circuits and battery power supply are all located within transmitter case 33, which is located in the upper left shoulder area in the same location as an implantable cardiac defibrillator or pacemaker metal case. An ECG sense positive lead wire 40 and ECG sense negative lead wire 42 are installed subcutaneously by an electrophysiologist for standard ECG monitoring. The ECG sensing and control circuits interpret signals from lead wires 40 and 42 and deliver the DC conduction block commands to optical transmitter 32. Optical transmitter case 33 serves as the ECG sensing circuit "return" path. Fiberoptic cable 44 generates an optical signal 48 that is received by one or more DC receivers 50, which convert the optical energy to a direct current and DC voltage. A receiver 50 will be attached to or embedded in body tissue or heart muscle, such as shown in FIG. 4. Typically receiver 50 will have a positive section 52 and a negative section 54 and there will be DC current flow from positive section 52 to negative section 54 through body tissue or heart muscle, which forms a "resistive load." Again, no batteries or other energy sources are required or deliver the DC conduction block at the sight of attachment.

The receiver 60 shown in FIGS. 2A and 2B can be any acceptable shape or geometry providing the device can be installed and anchored satisfactorily intracardially or epicardially. Each receiver 60, which is preferably straight or curved, comprises end sections 62 and a middle section 64. Middle section 64 comprises a hybrid receiver circuit 66 which is electrically connected through connectors 70 to anchor pins 72 in each end section 62. Optionally there may be an expansion/contraction zone 76 between middle section 64 and each end section 62, wherein the portion of connector 70 within zone 72 may comprise a spring 74.

Preferably each end section 62 and each anchor pin 72 comprises an electrically conducting, physiologically acceptable metal such as platinum, titanium, or stainless steel. There should be a sufficient number of anchor pins 72, for example, from about 4 to about 12, to anchor receiver 60 in proper position and transmit an RF or optical signal to body tissue or heart muscle.

Receiver 60 may have a polymeric outer surface 78 comprising polytetrafluoroethylene (TEFLON®) or a similar flexible, physiologically acceptable material. Also, receiver 60 is preferably from about 0.020 to about 0.025 in. in thickness and from about 0.30 to about 0.80 in. in length.

Spring expansion coils 74, such as are shown in FIGS. 2A and 2B, shall be a part of the design approach to accommodate heart beat activity and motion. The RF transmitter/receiver circuits 2, 16, 32, 50, and 60 shall have a fundamental frequency of about 1 GHz or higher with a sufficiently wide bandwidth to ensure that all of the receivers will detect the microwave signal at all times. Frequency and bandwidth will be carefully selected as not to receive interference from unwanted outside sources. Optical transmitter 32 shall have a sufficient light source with an acceptable light wavelength and frequency as to illuminate the pulmonary veins and the left atrium for a successful transfer of light energy into the optical receivers 50. Unlike a typical ICD, the RF or optical DC receiver 16 or 50 requires no battery or capacitor charging time and can deliver the first DC conduction blocking pulse instantaneously. This technique will be very useful and well tolerated by patients who require a rapid, atraumatic and painless prevention or conversion of AF/AFL with this device. This technology will use a fraction of the power of traditional ICD devices, thus enhancing battery life.

The transmitter antenna 6 or fiber optic cable or light pipe 36 will need to be in close proximity to the respective receiver 16 or 50 for optimum performance due to RF/microwave or optical losses in human tissue. The DC voltage and current may be pulsed or strobed on and off at slightly higher power levels for intervention/conversion and then rolled back to a prevention/-maintenance voltage and current level.

Figure 3:
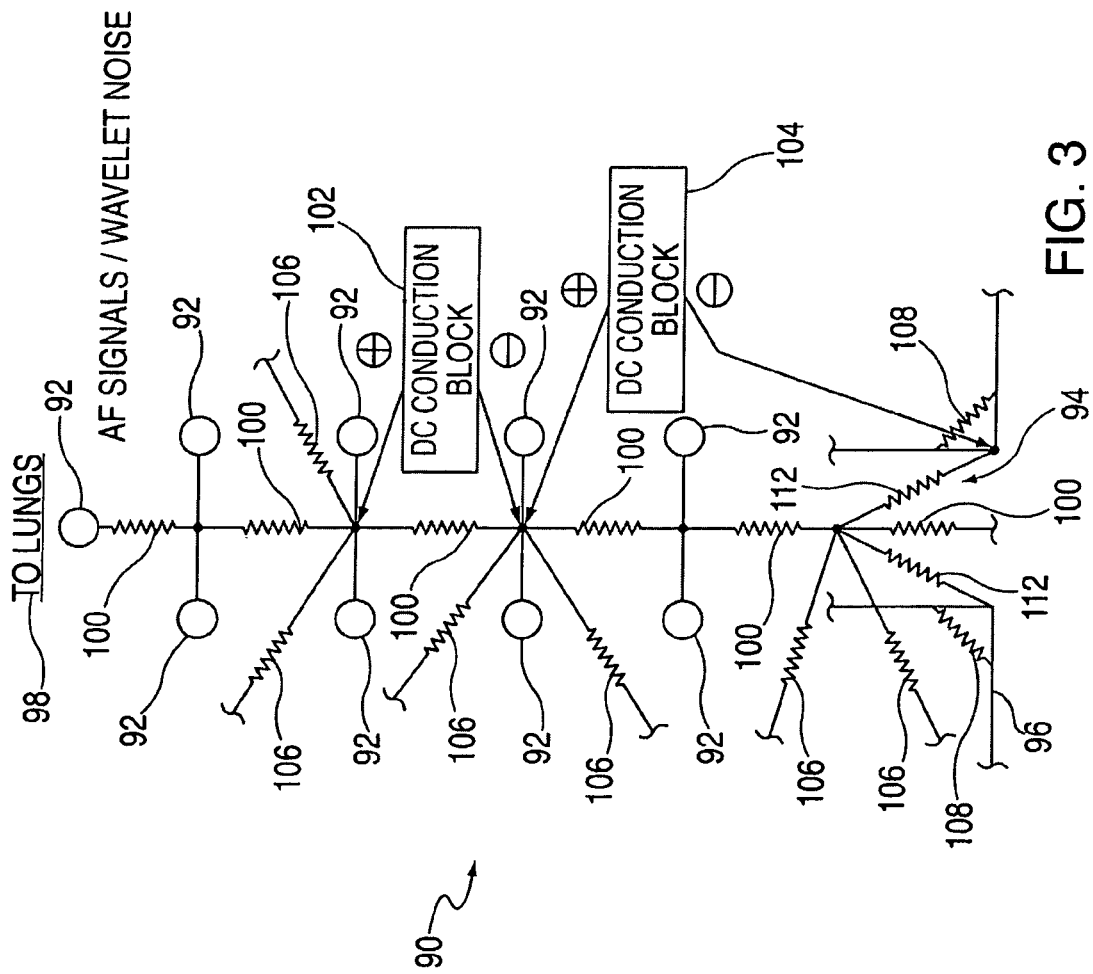
FIG. 3 is a schematic representation of an exemplary DC conduction block within a pulmonary vein as well as adjacent body tissue resistances.

FIG. 3 represents a schematic diagram of a resistive model 90 that shows where unwanted AF/AFL electrical signals 92 emanate from a pulmonary vein 94, which is connected to the lungs 98 at the distal end of pulmonary vein 94. As the unwanted signals propagate through pulmonary vein 94 into the left atrium 96, they are known to cause unwanted cardiac electrical stimulation which causes AF/AFL. The resistive schematic 100 depicts unwanted AF/AFL signals potentially emanating from any point along the entire length of pulmonary vein 94. Also, depicted are proposed DC conduction blocks 102 and 104 that will provide two primary functions that will affect terminating AF/AFL in a human heart. First, the entire wall of pulmonary vein 94 is intentionally saturated with DC current and voltage at low power between two contact points on or near pulmonary veins 94. This first element of noise cancellation provides new electrical pathways outside pulmonary vein 94 that are labeled "BT" or adjacent body tissue 106. These new pathways are where much of the unwanted AF/AFL signals will be allowed to dissipate into and away from pulmonary vein 94, fat pads 108, and left atrium 96 into adjacent tissue outside of the heart where the unwanted noise is harmless.

Secondly, as depicted in FIG. 4, pulmonary vein 94 has a transitional nature whereby pulmonary vein tissue 114 traversing from the lungs transitions and blends with left atrium 96 heart muscle at the zone where pulmonary vein 94 enters left atrium 96. The benefit of a DC conduction block between the pulmonary vein, fat pad, and left atrium is the physiologic property of heart muscle whereby the muscle tissue 112 is polarized in one direction, due to the presence of DC voltage and current through the pulmonary vein 94 and the fat pads 108, and returns through left atrium 96. When a DC current is applied in such a fashion or method, the pulmonary vein 94/left atrium 96 junctional area which may include the fat pads 108 is unable to react to the unwanted AF/AFL signals 92 that may be present. The DC conduction block overpowers the lower level AF/AFL signal potentials 92 thereby canceling the unwanted signals 92.

Fat pads 108 typically do not surround the pulmonary veins 94. Fat pads 108 contain nerves and ganglia but do not directly give rise to cardiac activation wavefronts that are conducted into the left atrium. Moreover, the nerves in fat pads 108 innervate heart muscle 112 and can affect the wavefronts within the heart muscle 112.

Thus, two important electrical principles are at work simultaneously. First, unwanted AF/AFL 92 signals are diverted off into adjacent tissues, body tissue 106 for dissipation via new DC current paths. And second, muscle tissue in and around pulmonary vein 94 and left atrium 96 cannot "fibrillate", "oscillate" or respond to the minor AF/AFL 92 signals due to the DC conduction blocks 102 and 104. The nerve cell membranes within the construct of the pulmonary veins are affected where the cathode is depolarized while the nerve cell membranes near an anode are hyperpolarized, inducing a DC conduction block 102 or 104.

Figure 5A:
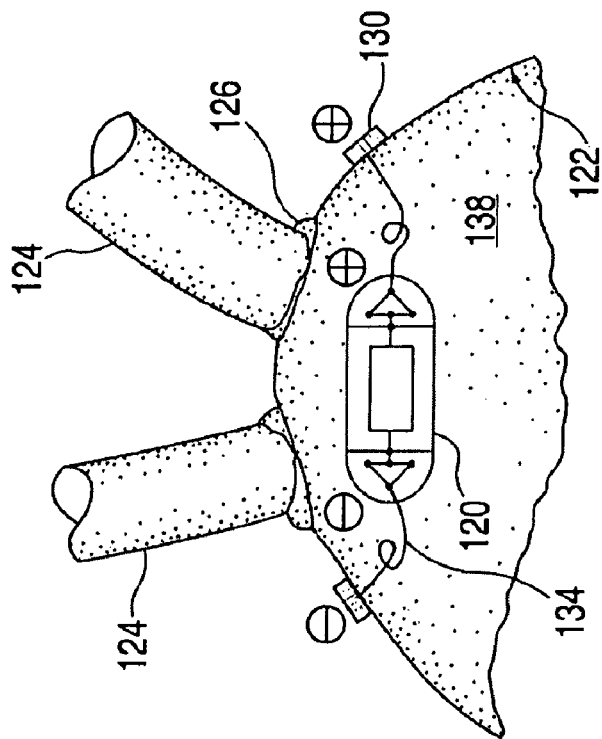
FIGS. 5A to 5C are each a mechanical and schematic representation of preferred epicardial attachment methods of RF or optical receivers.
Figure 5B:
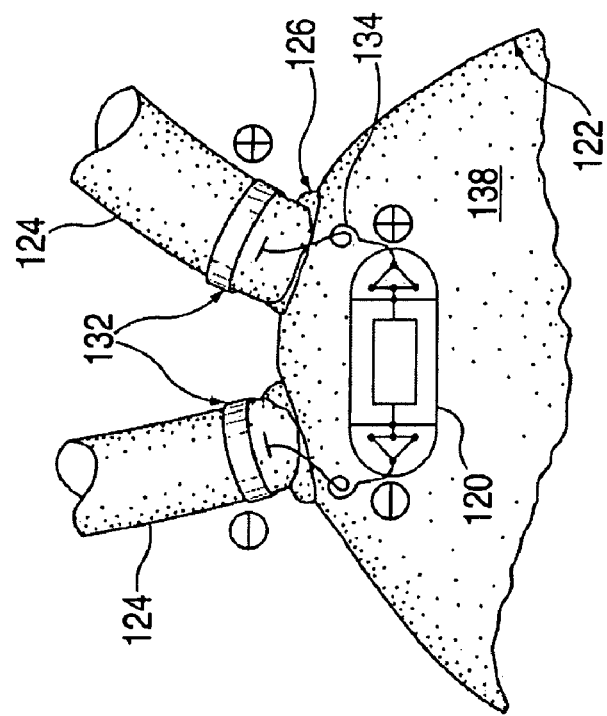
Figure 5C:
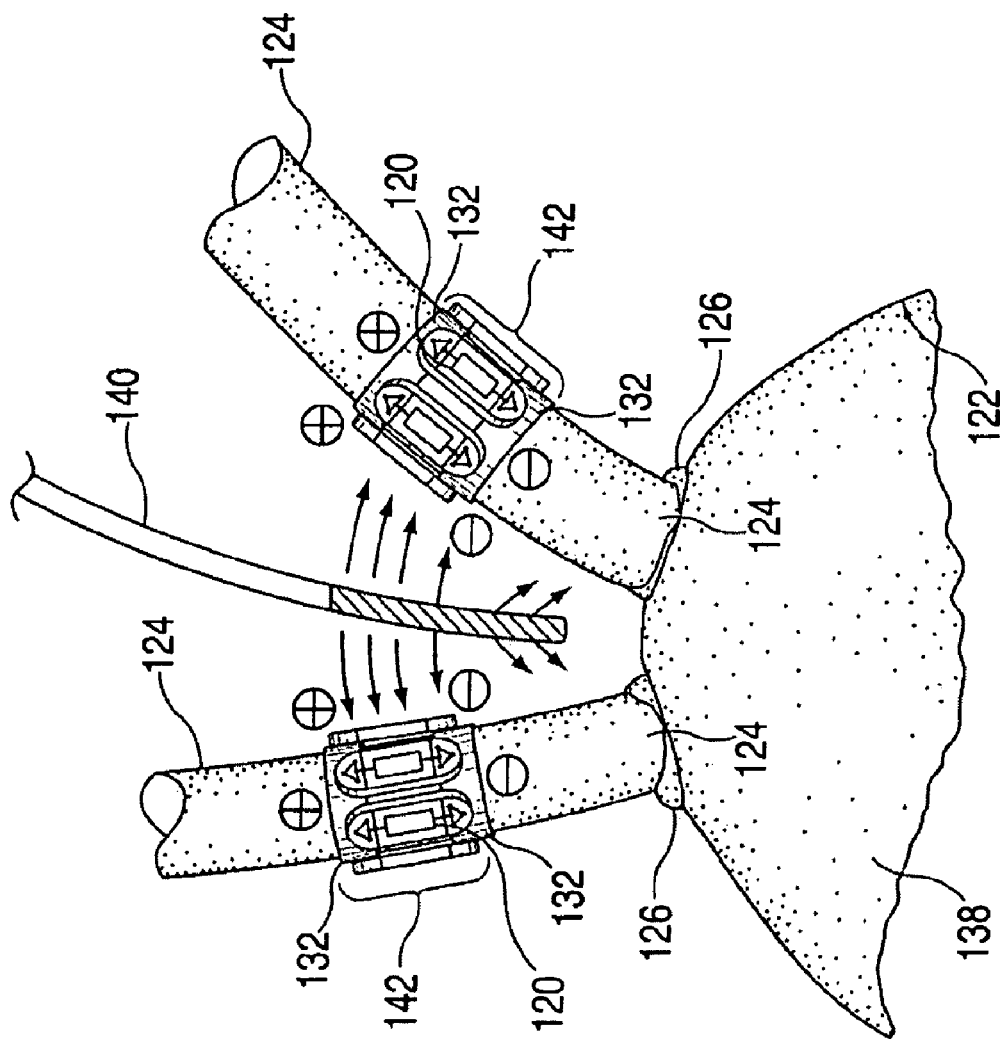

FIGS. 5A, 5B, and 5C depict typical epicardial installation and mechanical mounting of RF or optical receiver assemblies or devices 120 on the left atrium 122 in close proximity to the pulmonary veins 124 and fat pads 126 using platinum contact pads and anchor pins 130 or platinum contact pads 132. Several embodiments of similar positions and attachments are anticipated. Spring expansion coils 134 shall be a part of the design approach to accommodate heart beat activity and motion. The enlarged or stretched ostium 138 and left atrium 122 or entrance to pulmonary veins 124 within left atrium 122 are typical of structural heart disease due to abnormally high intra left atrium blood pressure over an extended time period during AF/AFL. Left atrium 122 wall thickness is compromised as being very thin, and electrical contacts will be designed to accommodate these deficiencies. The embodiment shown in FIG. 5C depicts an RF antenna or fiberoptic or light pipe transmitter 140 and an interventional and a preventative maintenance DC conduction block 142 for AF/AFL. DC receivers 120 may be attached directly between a short section approximately ⅛ to ½ inch of each pulmonary vein 124 epicardially via a limited thoracotomy for the purpose of creating individual DC conduction blocks for each pulmonary vein.

This system will be easily installed via a limited thoracotomy and the devices can be simply removed at a later date if required with a favorable and short surgery time allocation.

Figure 6:
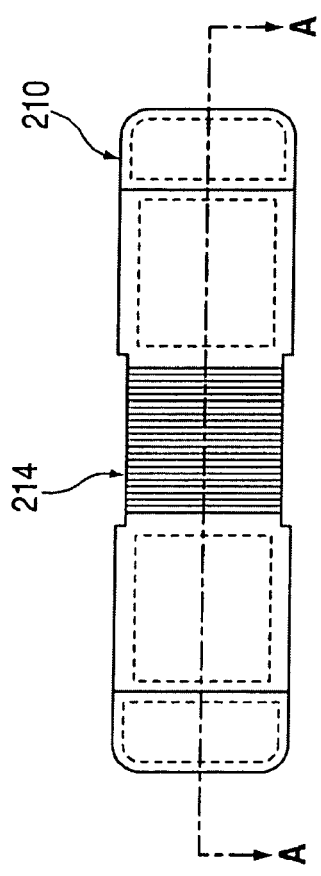
FIG. 6 is an electromechanical representation of a magnetic neurostimulator useful according to the invention.
Figure 7:
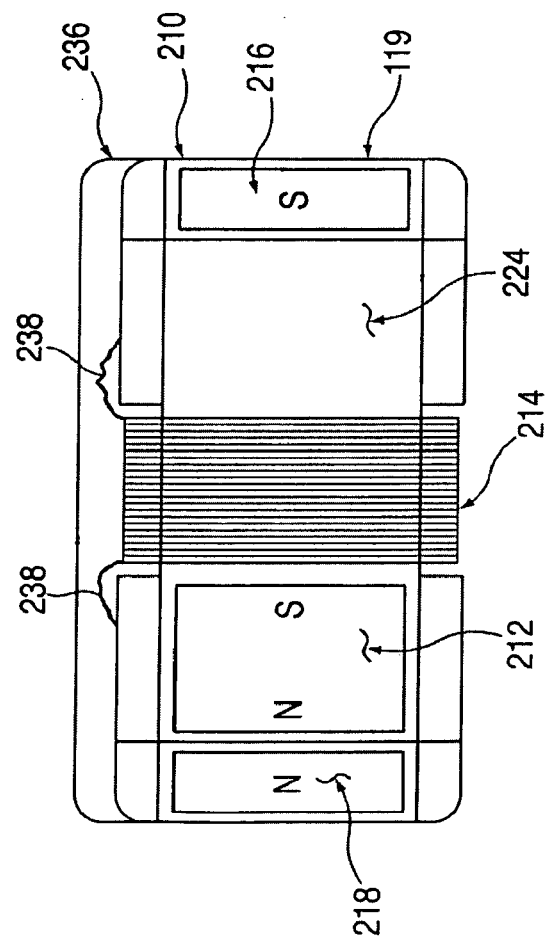
FIG. 7 is a cross-sectional view along line A-A of the magnetic neurostimulator shown in FIG. 6.

FIGS. 6 to 12A refer to a magnetic neurostimulator [MNS] device 210 in which a traversing or flying magnet 212 is employed using Faraday's Law of Electromotive Force [EMF] to create an electrical potential or voltage by moving a magnet through a coil 214 of wire with a specified number of turns. The traversing magnet 212 is captured in a cavity between two other magnets which are installed in fixed positions as to have their fields aligned as repelling magnets 216, 218 for the traversing magnet 212. On one end of the device the north pole of a fixed magnet 218 will be opposing the north pole of the traversing magnet 212 and on the opposite end of the device the south pole of the fixed magnet 216 will be opposing the south pole of the traversing magnet 212. This arrangement provides a traversing magnet 212 which will traverse or fly between both opposing fields within the device cavities without hitting the internal end walls of a case 222. [Magnetic poles or fields which are the same will repel and magnetic poles or fields which are opposites will attract.] Traversing magnet 212 shall have a coating of polytetrafluoroethylene or a similar material to reduce friction to near zero within the traversing chamber 224. As the traversing magnet 212 is propelled by the beating heart, walking, running or any other motion in the vectored direction of the device, the traversing magnet 212 passes through the wire coil 214 as shown in FIG. 6.

The repelling magnets 216, 218 aid in the perpetual motion of the traversing magnet as to provide a DC conduction block voltage even when a person is asleep or at rest. This action produces an electrical alternating current [AC] which is then rectified through BR1 230 into a direct current [DC]. The DC voltage is then filtered by C1 232 to remove any AC ripple and is also used as a storage device and keeps the DC voltage stable and quiet from noise to power the neurostimulator. Zener diode Z1 234 is used as an electrical clamp to keep the maximum voltage limited to a value expected to be from about 1 VDC to about 2 VDC. These components are housed in the electronics cavity 236. Coil wires 238 extend from wire coil 214 into electronics cavity 236.

Figure 8:
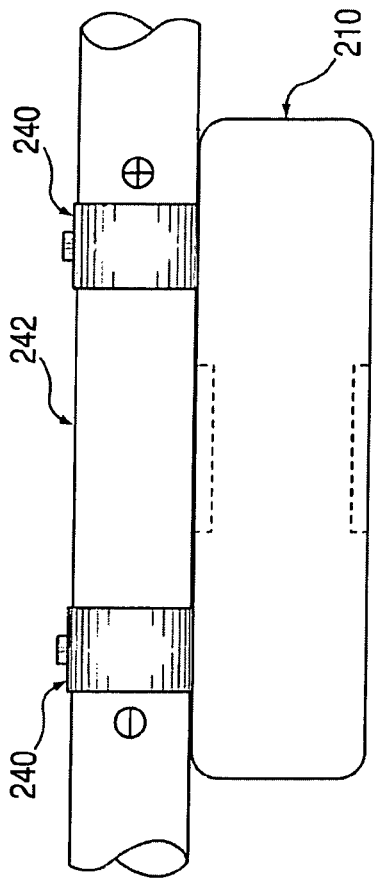
FIGS. 8 to 10 depict different views of a magnetic neurostimulator that is attached to a pulmonary vein epicardially in close proximity to the left atrium.
Figure 9:
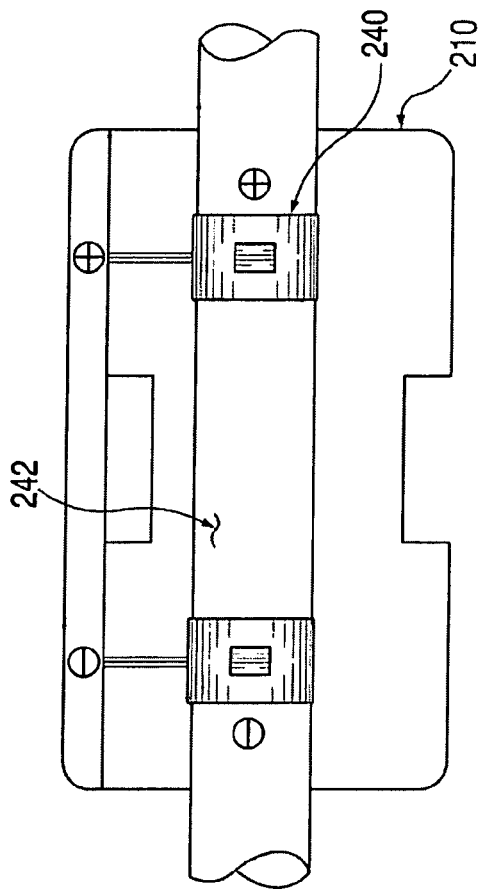
Figure 10:
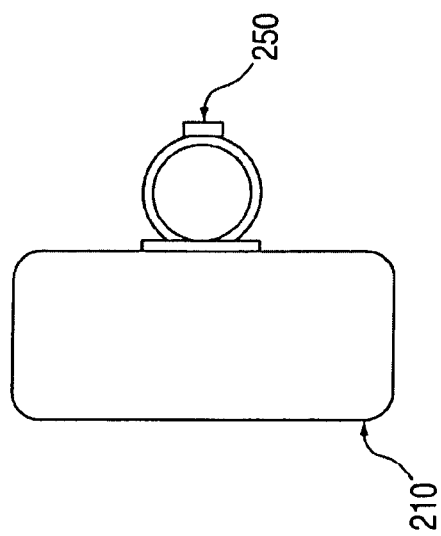
Figure 11:
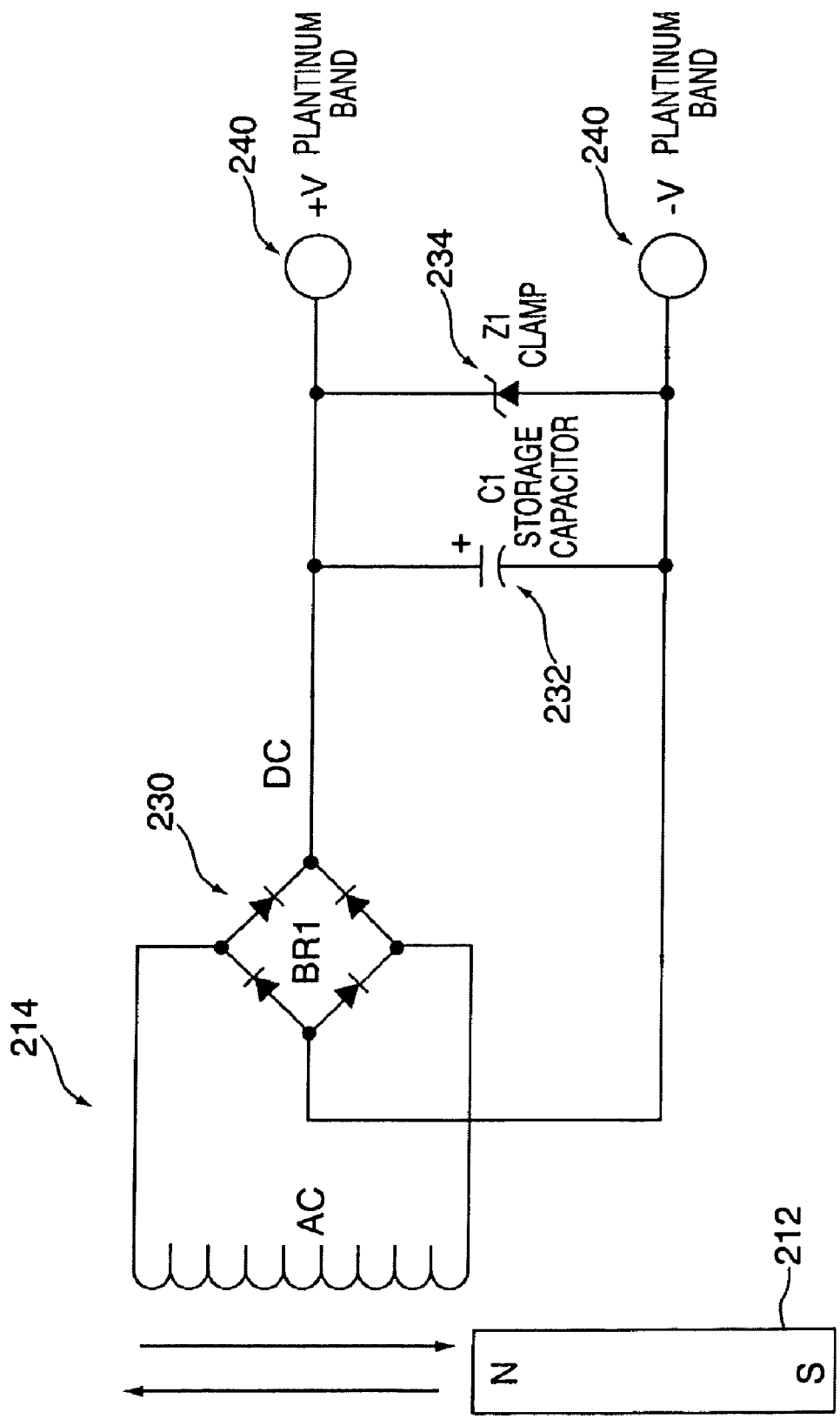
FIG. 11 is a schematic representation of a magnetic neurostimulator and the components that convert the AC voltage to a DC voltage.

When the heart is at a resting rate of from about 60 to about 80 beats per minute, the device will produce a modest voltage stimulus of from about 1 mVDC to about 500 mVDC. When the heart rate is increased through exercise above about 100 beats per minute, the expected voltage will rise to from about 1 VDC to about 2 VDC until Zener diode Z1 234 clamps the voltage at the selected peak voltage. These voltages provide a conduction block delivered to the platinum bands 240 anchored as shown in FIGS. 8 and 12 to the pulmonary veins 242 exiting the LA 244 and ostium 246. Advantageously, the magnetic device MNS 210 will prevent and convert atrial fibrillation without the use of any batteries, wires or outside energy source by creating an electrical conduction block between a small section of each pulmonary vein 242. The device is designed to provide an increased blocking voltage with increasing heart rate to block any micro-re-entrant wavelet noise that may be trying to conduct through the nerve cables within the pulmonary veins 242. Also, advantageously, in the prevention mode, as a person exercises and the heart rate in beats per minute increases, the output voltage of the MNS 210 increases, thereby providing an increased blocking voltage that will be protective against any initiated atrial fibrillation or atrial tachycardia stimulus or episode that has its origins emanating through the pulmonary veins 242.

Figure 12A:
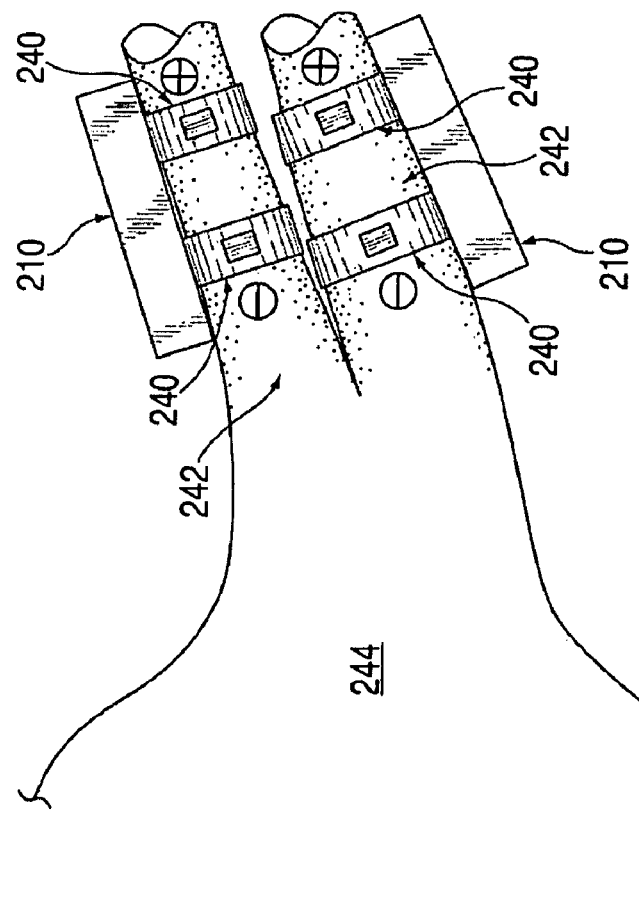
FIG. 12A is a mechanical representation of a preferred epicardial attachment method for a magnetic neurostimulator that involves attachment to exemplary abnormal, stretched, and distorted pulmonary veins.
Figure 12:
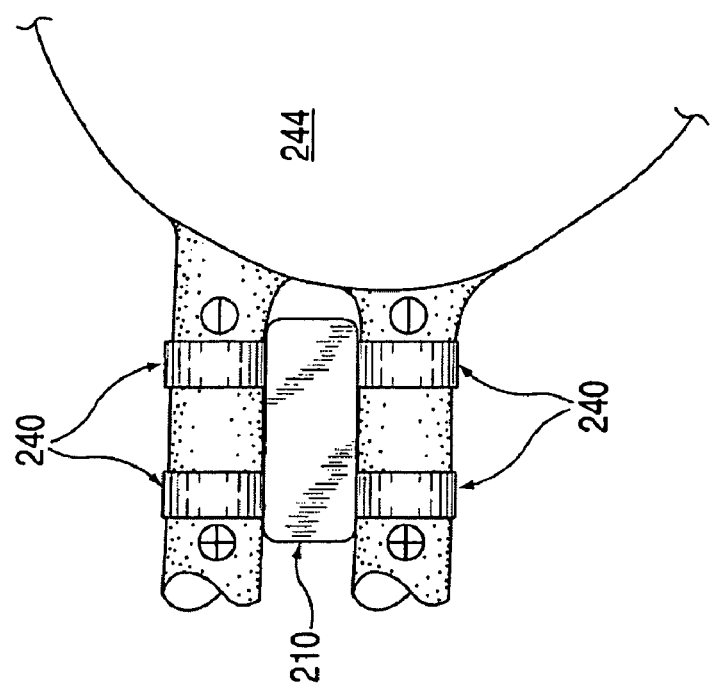
FIG. 12 is a mechanical representation of a preferred epicardial attachment method for a magnetic neurostimulator that involves an exemplary and normal attachment method onto pulmonary veins.

FIGS. 12 and 12A depict a wide range of sizes and shapes for pulmonary vein 242 and ostium 246 anatomy and the installation possibilities that may be employed to attach the MNS 210 device. Further, a cylindrical, oval or any other geometry magnet assembly may be employed in favor of the rectangular embodiment to facilitate the surgeon for rapid placement and attachment via limited thoracotomy through the inter-coastal spaces between the ribs. The MNS 210 device is attached to the pulmonary veins 242 via platinum bands 240 or equivalent which shall have an adjustment mechanism 250 as to firmly make contact with the circumference surface of the pulmonary veins 242 without causing any stenosis, distortion, or damage to the pulmonary veins 242. The MNS 210 may be anchored further by the surgeon mechanically to surrounding tissue within the pericardium if further attachment support is required for stability. Also, using the MNS 210 device, there is no requirement for any ECG sensing and control circuits, battery, metal case or any other device that supplies power to the MNS 210. This technology provides all of its own power requirements needed to deliver a DC conduction blocking device for the purpose of preventing or converting AF/AFL.

The goals and benefits of the technology of the invention are to prevent and convert patients with AF/AFL in an atraumatic method that have no hope of otherwise living with a normal cardiac sinus rhythm. Also, eliminating severe DC shocks for defibrillation and most pharmaceuticals such as blood thinners and anti-arrhythmic drugs which have untoward side affects. The patient would be able to better tolerate a soft conversion and prevention device that would cancel unwanted electrical activity which causes AF/AFL using a wireless DC device rather than electrically shocking the entire heart with intra-cardiac wires and high current DC pulses to defibrillate the heart back into a normal sinus rhythm.

Practical use of this technology may be accomplished in a hard wired, RF wireless or optical embodiment. In a hard wire configuration, a small, flat, helical, spiral, flexible printed circuit would be installed epicardially via limited thoracotomy and would flex in all relevant axis, otherwise known as the "six degrees of freedom," pitch, yaw, and roll. The proximal end of the flexible circuit would connect to the metal case housing the battery, and ECG sensing circuitry and the distal end would attach to the heart in the same fashion as the RF or optical receiver devices. The decision to use either embodiment would be made by an electrophysiologist.

The preceding specific embodiments are illustrative of the practice of the invention. It is to be understood, however, that other expedients known to those skilled in the art or disclosed herein, may be employed without departing from the spirit of the invention or the scope of the appended claims.

I claim:

1. A method for treating an electrical problem in a human or animal patient's heart having a left atrium which comprises atraumatically blocking the transmission of one or more electrical signals from a pulmonary vein, a fat pad, or a pulmonary vein and a fat pad from reaching the left atrium of the heart, wherein the one or more electrical signals are blocked by a DC current, voltage, or both DC current and voltage transmitted from an optical or light energy source to at least one noise cancellation device positioned on or adjacent to a pulmonary vein or a fat pad connected to the left atrium.

2. The method of claim 1, wherein nerve cell membranes near a cathode are depolarized while nerve cell membranes near an anode are hyperpolarized, inducing a DC conduction block.

3. The method of claim 1, wherein the DC current, voltage, or DC current and voltage results from a neurostimulator.

4. The method of claim 1, wherein the electrical signals are cancelled, redirected, or both.

5. A system for carrying out the method of claim 1, comprising:
a source of light or optical energy,
a transmitter for transmitting said energy; and
a receiver capable of receiving said energy and using said energy to block electrical signals from a pulmonary vein, a fat pad, or a pulmonary vein and a fat pad from reaching the left atrium of the heart,
wherein the one or more electrical signals are blocked by a DC current, voltage, or both DC current and voltage transmitted from an optical or light energy source.

6. The device of claim 5, wherein the electrical signals are cancelled, directed away from the heart, or a combination thereof.

7. The method of claim 1, wherein the electrical problem is atrial tachycardia, atrial fibrillation, or atrial flutter.

8. The method of claim 7, wherein the atrial flutter is typical atrial flutter or atypical atrial flutter.

9. The method of claim 1, wherein the one or more electrical signals are blocked so that they do not interfere with electrical signals from an SA node and/or the atrial electrical conduction system.

10. A system for treating a cardiac condition in a patient, which comprises:
an ECG sensing and control circuit;
a transmitter for transmitting an optical or light energy signal; and
at least one receiver for receiving said signal,
wherein each receiver is positioned on or adjacent to a pulmonary vein or fat pad and each receiver acts to cancel unwanted electrical signals from the pulmonary vein or fat pad to block the signals from reaching the left atrium of the patient's heart.

11. The system of claim 10, wherein the receiver is a neurostimulator.

12. The system of claim 10, wherein nerve cells near a cathode band or electrode are depolarized and nerve cells near an anode band or electrode are hyperpolarized.

13. The system of claim 12, wherein the nerves are within, on, or within and on the surface of pulmonary veins, between two electrical contacts or points.

14. The system of claim 10, which comprises a flexible circuit which is hard wired between the ECG sensing and control circuit and the targeted area for noise cancellation on the heart epicardially.

15. The system of claim 14, wherein the hard wired ECG and control circuits circuit are a neurostimulator.

16. A system for treating a cardiac condition in a patient, which comprises a magnetic neurostimulator comprising two fixed magnets, a traversing magnet, and a wire coil, wherein the traversing magnet oscillates back and forth through the wire coil thereby inducing an alternating current which is rectified through semiconductor diodes to form a direct current electrical voltage and current which comprises a conduction blocking signal wherein each magnetic device is positioned on a pulmonary vein and each magnetic neurostimulator acts to cancel unwanted electrical signals from a pulmonary vein or fat pad to block the signals from reaching the left atrium of the patient's heart.

17. The system of claim 16, wherein the traversing magnet DC power supply delivers a DC conduction block as a self-contained power supply or power source for delivery of the DC conduction block.

18. The system of claim 17, wherein the DC conduction block voltage and current increase and decrease as the heart rate increases and decreases in a human heart within medically therapeutic ranges to convert or prevent atrial fibrillation or atrial tachycardia.

19. The system of claim 18, wherein the traversing magnetic power supply provides increased prevention and protection from atrial fibrillation or atrial tachycardia via the heart rate increase causing an increasing neurostimulator output voltage and current up to a predetermined and clamped level while also providing prevention and conversion for atrial fibrillation or atrial tachycardia when the heart is at rest or beating at slower rates.

* * * * *